(12) United States Patent
Takahashi et al.

(10) Patent No.: US 7,345,164 B2
(45) Date of Patent: Mar. 18, 2008

(54) PRODUCTION METHOD OF 5'-ACYLOXYNUCLEOSIDE COMPOUND

(75) Inventors: Daisuke Takahashi, Kawasaki (JP); Kunisuke Izawa, Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 591 days.

(21) Appl. No.: 10/829,950

(22) Filed: Apr. 23, 2004

(65) Prior Publication Data

US 2004/0230053 A1 Nov. 18, 2004

(30) Foreign Application Priority Data

Apr. 25, 2003 (JP) ............................. 2003-121551

(51) Int. Cl.
*C07H 19/067* (2006.01)
*C07H 19/167* (2006.01)

(52) U.S. Cl. ................................ 536/27.11; 536/27.21; 536/28.4

(58) Field of Classification Search ............. 536/27.11, 536/27.21, 28.4
See application file for complete search history.

(56) References Cited

U.S. PATENT DOCUMENTS

| | | | |
|---|---|---|---|
| 2004/0230053 A1* | 11/2004 | Takahashi et al. | 536/26.71 |
| 2005/0137404 A1 | 6/2005 | Takahashi et al. | |
| 2005/0165234 A1 | 7/2005 | Takahashi et al. | |
| 2005/0176966 A1 | 8/2005 | Takahashi et al. | |
| 2005/0209257 A1 | 9/2005 | Takahashi et al. | |
| 2005/0215789 A1 | 9/2005 | Takahashi et al. | |
| 2006/0270850 A1 | 11/2006 | Takahashi et al. | |

OTHER PUBLICATIONS

[R] Smith et al., "March's Advanced Organic Chemistry, 5th Edition," Wiley-Interscience, New York, NY, 2001, only pp. 450-454 supplied.*
A. Kumar, et al., Tetrahedron, vol. 46, No. 9, pp. 3101-3110, "The Chemistry of 2', 3'-Seconucleosides IV. Synthesis and Reactions of 3'-Azido-2',3'-Dideoxy-2',3'-Secothymidine and Related Analogues", 1990.
B. E. Griffin, et al., Tetrahedron, vol. 23, No. 5, pp. 2301-2313, "The Synthesis of Oligoribonucleotides-II, Methoxymethylidene Derivatives of Ribonucleosides and 5'-Ribonucleotides", 1967.
Y. Ishido, et al., Journal of the Chemical Society Perkin Transaction, pp. 563-573, "Partial Protection of Carbohydrate Derivatives. Part 4. Regioselective 2'-O-Deacylation of Fully Acylated Purine and Pyrimidine Ribonucleosides with Hydroxylaminium Acetate", 1980.

S. Nishino, et al., Tetrahedron, vol. 41, No. 23, pp. 5503-5506, "Partial Protection of Carbohydrate Derivatives. Part 18. Simple, Preparative Procedure for 5'-O-Acylribonucleosides; Highly Regioselective O-Deacylation at 2' and 3' Positions of Fully Acylated Purine and Pyrimidine Ribonucleoside Through Sodium Methoxide-THF System", 1985.
Morris J. Robins, et al., "Nucleic Acid Related Compounds. 114. Synthesis of 2,6-(Disubstituted))Purine 2',3'-Dideoxynucleosides and Selected Cytotoxic, Anti-Hepatitis B, and Adenosine Deaminase Substrate Activities", Journal of Heterocyclic Chemistry, Hetero Corp., XP-002952782, vol. 38, Nov. 2001, pp. 1297-1306.
Fung-Lung Chung, et al., Synthesis of 5-Amino-9-(β-D-Ribofuranosyl)-v-triazino[4,5-b]-Pyrimido[4,5-d]pyrrol-4-one and Unusual Ring Opening of This New Ring System with the Vilsmeier-Haack Reagent, Journal Org. CHEM., XP-002292937, vol. 45, 1980, pp. 2532-2535.

* cited by examiner

*Primary Examiner*—L. E. Crane
(74) *Attorney, Agent, or Firm*—Oblon, Spivak, McClelland, Maier & Neustadt, P.C.

(57) ABSTRACT

A production method for conveniently producing a 5'-acyloxynucleoside compound shown by the formula [A] in a good yield while suppressing formation of by-products, including subjecting a 2',3',5'-triacyloxynucleoside compound represented by the formula [I] to selective deacylation in an alcohol represented by the formula [II] using a base selected from the group consisting of alkali metal hydroxide, alkali metal alkoxide and alkali metal carbonate:

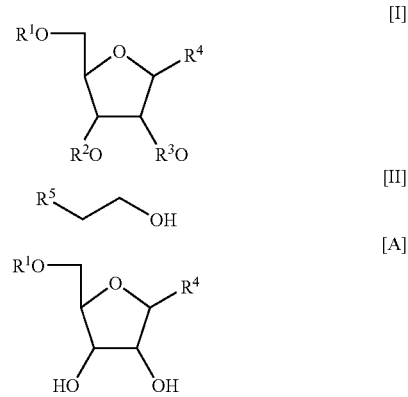

wherein each symbol in the formula is as defined in the specification.

7 Claims, No Drawings

PRODUCTION METHOD OF 5'-ACYLOXYNUCLEOSIDE COMPOUND

CROSS-REFERENCE TO RELATED APPLICATIONS

The present application claims priority to JP 2003-121551, filed on Apr. 25, 2003.

TECHNICAL FIELD OF THE INVENTION

The present invention relates to a production method of a 5'-acyloxynucleoside compound.

BACKGROUND OF THE INVENTION

A 5'-acyloxynucleoside compound represented by the formula

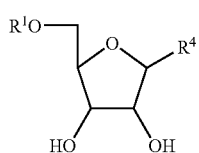

[A]

wherein $R^1$ is an acyl group and $R^4$ is

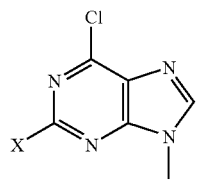 or 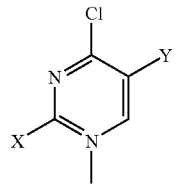

wherein X is a hydrogen atom, a halogen atom, an amino group, an alkyl group, an aralkyl group, a substituted amino group or a hydroxyl group, and Y is a hydrogen atom, a halogen atom, an alkyl group, an aralkyl group or an aryl group is useful for the production of a deoxynucleic acid derivative and the like.

As a production method of the 5'-acyloxynucleoside compound, for example, a method comprising protecting hydroxyl groups at the 2- and 3-positions with isopropylidene groups and the like, protecting a hydroxyl group at the 5'-position with an acyl group such as benzoyl group, acetyl group and the like, and removing isopropylidene groups has been reported (Tetrahedron, vol. 46, No. 9, p. 3101 (1990), and Tetrahedron, vol. 23, No. 5, pp. 2301-313 (1967)). This method is problematic in that the operation is complicated and the number of steps is many.

In addition, a method comprising selective deacylation of a nucleic acid derivative (nucleoside) with hydroxylamine acetate/pyridine (Journal of the Chemical Society Perkin Transaction, pp. 563-573 (1980)), and a method comprising selective debenzoylation of a nucleic acid derivative with tetrahydrofuran/sodium methoxide (Tetrahedron, No. 41, vol. 23, pp. 5503-5506 (1985)) have been reported. These methods are problematic in that a pyridine adduct is by-produced in the former and a methoxy form is by-produced in the latter, which markedly degrades the yield.

Thus, there is a demand for a method for conveniently producing a 5'-acyloxynucleoside compound in a good yield while suppressing formation of by-products.

SUMMARY OF THE INVENTION

It is therefore an object of the present invention to provide a method for conveniently producing a 5'-acyloxynucleoside compound in a good yield while suppressing the formation of by-products.

According to the present invention, it has now been found that, by subjecting a 2',3',5'-triacyloxynucleoside compound represented by the formula [I] below to deacylation using a base selected from the group consisting of alkali metal hydroxide, alkali metal alkoxide and alkali metal carbonate, in an alcohol represented by the formula [II], the deacylation proceeds selectively, thereby resulting in the convenient roduction of a 5'-acyloxynucleoside compound in a good yield while suppressing the formation of by-products.

Accordingly, the present invention provides the following.

(1) A production method of a 5'-acyloxynucleoside compound represented by the formula [A]

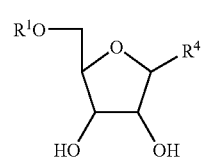

[A]

wherein $R^1$ is an acyl group, and $R^4$ is

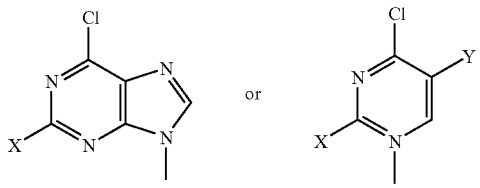 or wherein X is a hydrogen atom, a halogen atom, an amino group, an alkyl group, an aralkyl group, a substituted amino group or a hydroxyl group, and Y is a hydrogen atom, a halogen atom, an alkyl group, an aralkyl group or an aryl group, which comprises subjecting a 2',3',5'-triacyloxynucleoside compound represented by the formula [I]

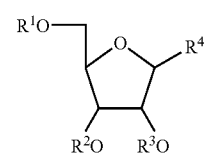

[I]

wherein $R^1$ is as defined above, $R^2$ and $R^3$ are the same or different and each is independently an acyl group, to selective deacylation in an alcohol represented by the formula [II]

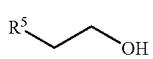

wherein R⁵ is a hydrogen atom, an alkoxy group or an optionally substituted aryloxy group, using a base selected from the group consisting of alkali metal hydroxide, alkali metal alkoxide and alkali metal carbonate.

(2) The production method of (1) above, wherein the alcohol represented by the formula [II] is used in a 1- to 50-fold weight ratio relative to the 2',3',5'-triacyloxynucleoside compound represented by the formula [I].

(3) The production method of (1) or (2) above, wherein the alcohol represented by the formula [II] is selected from the group consisting of ethanol, 2-methoxyethanol and 2-butoxyethanol.

(4) The production method of (1) above, wherein the base is used in a 0.01- to 0.5-fold molar ratio relative to the 2',3',5'-triacyloxynucleoside compound.

(5) The production method of (1) above, wherein the base is selected from the group consisting of sodium hydroxide, sodium ethoxide and potassium carbonate.

(6) The production method of (1) above, wherein the 5'-acyloxynucleoside compound represented by the formula [A] is 5'-acetyl-6-chloropurine riboside.

DETAILED DESCRIPTION OF THE INVENTION

The present invention is explained in detail in the following.

In the present invention, $R^1$, $R^2$ and $R^3$ may be the same or different and each is independently an acyl group. The acyl group here is an acyl group generally having 1 to 20, preferably 2 to 8, carbon atoms. Examples thereof include acetyl, propionyl, benzoyl and the like, with preference given to acetyl.

The X in the present invention means a hydrogen atom, a halogen atom, an amino group, an alkyl group, an aralkyl group, a substituted amino group or a hydroxyl group, and Y means a hydrogen atom, a halogen atom, an alkyl group, an aralkyl group or an aryl group.

As used herein, the halogen atom is a chlorine atom, a fluorine atom, a bromine atom or an iodine atom, which is preferably a chlorine atom for X and Y.

As used herein, the alkyl group is a linear or branched chain alkyl group preferably having 1 to 10, more preferably 1 to 3, carbon atoms. For example, a methyl group, an ethyl group, a propyl group and the like can be mentioned, with preference given to methyl.

As used herein, the aralkyl group is that wherein the alkyl moiety is a linear or branched chain preferably having 1 to 5, more preferably one, carbon atom, and the aryl moiety preferably has 6 to 10, more preferably 6 to 8, carbon atoms. Preferable examples include benzyl and the like.

As used herein, the aryl group preferably has 6 to 10, more preferably 6 to 8, carbon atoms. Preferable examples include a phenyl group and the like.

The substituted amino group means an amino group monosubstituted or disubstituted by the following substituent and the like. The disubstituted amino group may have the same substituents or different substituents. As the substituent, for example, an acyl group (preferably having 1 to 7 carbon atoms, such as acetyl, propionyl, benzoyl and the like, particularly preferably acetyl), an alkyl group (as defined above, particularly preferably methyl and ethyl), an aryl group (as defined above, particularly preferably phenyl), an aralkyl group (as defined above, particularly preferably benzyl) and the like can be mentioned. Examples of the substituted amino group include acetylamino, methylamino, ethylamino, phenylamino, benzylamino and the like, with preference given to acetylamino and benzylamino.

In the present invention, $R^5$ means a hydrogen atom, an alkoxy group or an optionally substituted aryloxy group. As used herein, the alkoxy group is a linear or branched chain alkoxy group preferably having 1 to 10, more preferably 1 to 4, carbon atoms. Examples thereof include methoxy, ethoxy, propoxy, n-butoxy and the like, with preference given to methoxy and n-butoxy.

As used herein, the optionally substituted aryloxy group has an aryl moiety as defined above, wherein the substituent is, for example, a halogen atom (as defined above) and the like. Specific examples include phenoxy, chlorophenoxy, bromophenoxy and the like, with preference given to phenoxy.

Production Method of 5'-acyloxynucleoside Compound

The production method of a 5'-acyloxynucleoside compound according to the present invention comprises subjecting a 2',3',5'-triacyloxynucleoside compound to selective deacylation in an alcohol of the formula [II] using a base selected from the group consisting of alkali metal hydroxide, alkali metal alkoxide and alkali metal carbonate.

To be precise, the above-mentioned specific base is added to a solution of a 2',3',5'-triacyloxynucleoside compound in the above-mentioned specific alcohol and the mixture is stirred. The base may be added as it is or added in the form of a solution.

As the solvent to be used for the production of a 5'-acyloxynucleoside compound is essentially an alcohol represented by the formula [II]

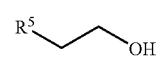

wherein $R^5$ is as defined above. In the present invention, the solvent to be selected from the alcohols may be one kind or two or more kinds.

Preferable alcohol of the formula [II] is selected from the group consisting of ethanol, 2-methoxyethanol and 2-butoxyethanol. For example, ethanol alone, a mixed solvent of ethanol and 2-methoxyethanol, a mixed solvent of ethanol and 2-butoxyethanol and the like can be mentioned. The amount of alcohol of the formula [II] to be used is preferably 1- to 50-fold, more preferably 2- to 10-fold, in weight ratio relative to 2',3',5'-triacyloxynucleoside compound.

The base to be used for the production of a 5'-acyloxynucleoside compound is essentially selected from the group consisting of alkali metal hydroxide, alkali metal alkoxide and alkali metal carbonate. As used herein, alkali metal hydroxide includes, for example, sodium hydroxide, potassium hydroxide and lithium hydroxide; alkali metal alkoxide includes, for example, sodium ethoxide, potassium butoxide and sodium methoxide; and alkali metal carbonate includes, for example, potassium carbonate, sodium carbonate and lithium carbonate. Of these, a base selected from the group consisting of sodium hydroxide, sodium ethoxide and potassium carbonate is preferable.

The amount of the base to be used is preferably 0.01- to 0.5-fold, more preferably 0.03- to 0.2-fold, in molar ratio relative to the 2',3',5'-triacyloxynucleoside compound.

As the solvent for adding a base in the form of a solution, any solvent other than water can be used without particular limitation. For example, the above-mentioned alcohol of the formula [II] may be used. When a base is added in the form of a solution, a base is dissolved in one or more kinds of these solvents to a concentration of preferably 1-30 weight %, more preferably 2-15 weight %. When an alcohol of the formula [II] such as ethanol, 2-methoxyethanol, 2-butoxyethanol and the like is used as a solvent, its amount is added to the above-mentioned "amount of alcohol of the formula [II] to be used".

The production of a 5'-acyloxynucleoside compound of the resent invention completes generally at $-10°$ C. to $40°$ C., preferably $0°$ C. to $15°$ C., generally immediately after the start of the reaction—10 hr later, preferably in 1-5 hr.

The 5'-acyloxynucleoside compound obtained by the method of the present invention can be isolated or purified by a conventional method. For example, a reaction solution is neutralized with an acid (e.g., acetic acid and the like), concentrated to dryness and the residue is applied to silica gel column chromatography.

The 2',3',5'-triacyloxynucleoside compound to be used as a starting material can be produced by, for example, the method described in Nucleic Acid Chem., 264-268 (1991). For example, 2',3',5'-triacetyl-6-chloropurine riboside, which is one of the starting materials, can be produced by adding dropwise thionyl chloride to 2',3',5'-triacetylinosine in a solvent, stirring the mixture under reflux, then working-up by conventional methods.

The 5'-acyloxynucleoside compound of the present invention can be introduced into a deoxynucleic acid compound having an antivirus activity according to the methods described in, for example, Synlett, 753 (1991) and J. Am. Chem. Soc., 111., 8502-8540 (1989) and the like.

EXAMPLES

The present invention is explained in detail in the following by referring to Examples, which are not to be construed as limitative.

Preparation Example 1

2',3',5'-triacetyl-6-chloropurine riboside

2',3',5'-Triacetylinosine (20 g) was added to chloroform (160 ml) and N,N-dimethylformamide (2.7 g), and thionyl chloride (19.9 g) was added dropwise. The mixture was stirred under reflux for 3 hr. Water (200 ml) was added and the mixture was stirred for 1 hr while cooling in an ice bath and partitioned. The organic layer was washed with 5% aqueous sodium hydrogen carbonate solution and saturated brine, dried over sodium sulfate and concentrated to dryness to give 2',3',5'-triacetyl-6-chloropurine riboside (24.4 g) as an oil. 2',3',5'-triacetyl-6-chloropurine riboside $^1$H-NMR(CDCl$_3$, ppm):δ 2.10(3H,s), 2.12(3H,s), 2.17 (3H,s), 4.37-4.51(3H,m), 5.64-5.67(1H,m), 5.94-5.97(1H, m), 6.24-6.25(1H,d,J=5.2 Hz), 8.30(1H,s), 8.79(1H,s).

Example 1

5'-acetyl-6-chloropurine riboside

2',3',5'-Triacetyl-6-chloropurine riboside (5.0 g, 12.1 mmol) was dissolved in 2-methoxyethanol (26 ml) and a 5 weight % sodium hydroxide-ethanol solution (0.4 g) was added under ice-cooling. The mixture was stirred for 4 hr. Acetic acid (0.1 g) was added and the reaction mixture was concentrated to dryness. The obtained oil was purified by silica gel column chromatography (methylene chloride—methanol) and concentrated to dryness to give the title compound (3.01 g, 9.1 mmol, 75%) as white crystals. 5'-acetyl-6-chloropurine riboside $^1$H-NMR(CDCl$_3$,ppm):δ 2.07(3H,s), 4.10(1H,d,J=5.2 Hz), 4.36-4.56(4H,m), 4.73-4.77(1H,m), 5.13(1H,d,J=4.4 Hz), 6.12(1H,d,J=4.0 Hz), 8.40(1H,s), 8.71(1H,s).

Example 2

5'-acetyl-6-chloropurine riboside

2',3',5'-Triacetyl-6-chloropurine riboside (830 mg) was dissolved in ethanol (4.5 ml) and a 5 weight % sodium hydroxide-ethanol solution (65 mg) was added under ice-cooling. The mixture was stirred for 4 hr. The reaction solution was analyzed by high performance liquid chromatography (HPLC), whereby production of the title compound in a yield of 77% was confirmed.

Example 3

5'-acetyl-6-chloropurine riboside

2',3',5'-Triacetyl-6-chloropurine riboside (820 mg) was dissolved in ethanol (4 ml) and potassium carbonate (56 mg) was added at room temperature. The mixture was stirred for 4 hr. The reaction solution was analyzed by HPLC, whereby production of the title compound in a yield of 77% was confirmed.

Example 4

5'-acetyl-6-chloropurine riboside

2',3',5'-Triacetyl-6-chloropurine riboside (520 mg) was dissolved in 2-butoxyethanol (3 ml) and 2 weight % of a sodium hydroxide-ethanol solution (44 mg) was added under ice-cooling. The mixture was stirred for 4 hr. The reaction solution was analyzed by HPLC, whereby production of the title compound in a yield of 82% was confirmed.

Example 5

5'-acetyl-6-chloropurine riboside

2',3',5'-Triacetyl-6-chloropurine riboside (830 mg) was dissolved in ethanol (4.5 ml) and 21-weight % of a sodium ethoxide-ethanol solution (26 mg) was added under ice-cooling. The mixture was stirred for 3 hr. The reaction solution was analyzed by HPLC, whereby production of the title compound in a yield of 76% was confirmed.

Reference Example 1

2',3',5'-Triacetyl-6-chloropurine riboside (655 mg) was dissolved in pyridine (4 ml) and hydroxylamine acetate (13 mg) was added under ice-cooling. The mixture was stirred for 4 hr. The reaction solution was analyzed by HPLC. As a result, 5'-acetyl-6-chloropurine riboside was not produced at all and production of 6-pyridylpurine riboside was confirmed.

Reference Example 2

2',3',5'-Triacetyl-6-chloropurine riboside (800 mg) was dissolved in tetrahydrofuran (4 ml) and sodium methoxide (158 mg) was added under ice-cooling. The mixture was stirred for 4 hr. The reaction solution was analyzed by HPLC. As a result, 5'-acetyl-6-chloropurine riboside was not produced at all and production of 6-methoxypurine riboside was confirmed.

INDUSTRIAL APPLICABILITY

According to the present invention, a 5'-acyloxynucleoside compound can be conveniently produced in a good yield while suppressing formation of by-product.

This application is based on a patent application No. 2003-121551 filed in Japan, the contents of which are hereby incorporated by reference. The references cited herein, including patents and patent applications, are hereby incorporated in their entireties by reference, to the extent that they have been disclosed herein.

What is claimed is:

1. A method of making a 5'-acyloxynucleoside compound represented by the formula [A]

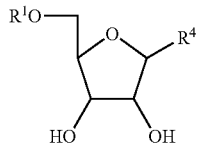

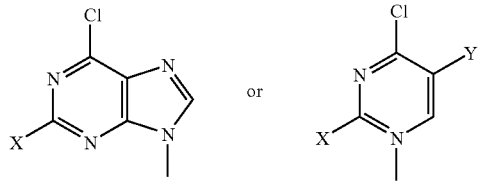

wherein $R^1$ is an acyl group, and $R^4$ is wherein X is a hydrogen atom, a halogen atom, an amino group, an alkyl group, an aralkyl group, a substituted amino group or a hydroxyl group, and Y is a hydrogen atom, a halogen atom, an alkyl group, an aralkyl group or an aryl group, which comprises contacting a 2',3',5'-triacyloxynucleoside compound represented by the formula [I]

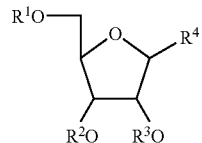

wherein $R^1$ is as defined above, $R^2$ and $R^3$ are the same or different and each is independently an acyl group, in an alcohol represented by the formula [II]

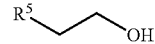

wherein $R^5$ is a hydrogen atom, an alkoxy group, an aryloxy group or an aryloxy group substituted with a halogen atom, with a base selected from the group consisting of alkali metal hydroxide, alkali metal alkoxide and alkali metal carbonate.

2. The method of claim 1, wherein the alcohol represented by the formula [II] is used present in a 1- to 50-fold weight ratio relative to the 2',3',5'-triacyloxynucleoside compound represented by the formula [I].

3. The method of claim 1, wherein the alcohol represented by the formula [II] is selected from the group consisting of ethanol, 2-methoxyethanol and 2-butoxyethanol.

4. The method of claim 1, wherein the base is present in a 0.01- to 0.5-fold molar ratio relative to the 2',3',5'-triacyloxynucleoside compound.

5. The method of claim 1, wherein the base is selected from the group consisting of sodium hydroxide, sodium ethoxide and potassium carbonate.

6. The method of claim 1, wherein the 5'-acyloxynucleoside compound represented by the formula [A] is 5'-acetyl-6-chloropurine riboside.

7. The method of claim 2, wherein the alcohol represented by the formula [II] is selected from the group consisting of ethanol, 2-methoxyethanol and 2-butoxyethanol.

* * * * *